US010376341B2

(12) United States Patent
Paehl (10) Patent No.: US 10,376,341 B2
(45) Date of Patent: Aug. 13, 2019

(54) LABIAL ATTACHMENT DEVICE FOR USE WITH ORTHODONTIC AUXILIARY AND LINGUAL APPLIANCE SYSTEM (71) Applicant: 3M INNOVATIVE PROPERTIES COMPANY, St. Paul, MN (US)

(72) Inventor: Ralf M. Paehl, Melle (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/101,977

(22) PCT Filed: Dec. 2, 2014

(86) PCT No.: PCT/US2014/068071
§ 371 (c)(1),
(2) Date: Jun. 6, 2016

(87) PCT Pub. No.: WO2015/084795
PCT Pub. Date: Jun. 11, 2015

(65) Prior Publication Data
US 2016/0302891 A1   Oct. 20, 2016

(30) Foreign Application Priority Data
Dec. 6, 2013   (EP) ..................................... 13195992

(51) Int. Cl.
*A61C 7/36*   (2006.01)
*A61C 7/28*   (2006.01)
*A61C 7/14*   (2006.01)

(52) U.S. Cl.
CPC ................ *A61C 7/36* (2013.01); *A61C 7/282* (2013.01); *A61C 7/145* (2013.01)

(58) Field of Classification Search
CPC ........... A61C 7/36; A61C 7/282; A61C 7/145; A61C 7/06; A61C 7/10; A61C 7/22
USPC ............................................. 433/19; 128/861
See application file for complete search history.

(56) References Cited

U.S. PATENT DOCUMENTS

| 4,708,646 | A | 11/1987 | Jasper |
| 5,352,116 | A | 10/1994 | West |
| 5,435,721 | A | 7/1995 | Vogt |
| 5,618,176 | A | 4/1997 | Andreiko |
| 5,651,672 | A | 7/1997 | Cleary |

(Continued)

FOREIGN PATENT DOCUMENTS

| CA | 2382912 | 4/2003 |
| DE | 19526474 | 1/1997 |

(Continued)

OTHER PUBLICATIONS

International Search report for PCT International Application No. PCT/US2014/068071 dated Feb. 27, 2015, 4 pages.

*Primary Examiner* — Wade Miles
*Assistant Examiner* — Drew S Folgmann (57) ABSTRACT The present disclosure provides an assembly and system allowing for secure use of an orthodontic auxiliary, particularly a bite corrector, with lingually bonded appliance systems. In one aspect, the disclosure features an orthodontic assembly including a banded tube, a force module, a connector coupling the force module to the tube, and an attachment device secured to the labial surface of an anterior tooth and connected to mesial, outer end of the force module.

6 Claims, 6 Drawing Sheets

(56) References Cited

U.S. PATENT DOCUMENTS

| | | |
|---|---|---|
| 5,718,576 A | 2/1998 | Schnaitter |
| 5,964,588 A | 10/1999 | Cleary |
| 6,113,390 A | 9/2000 | Sirney |
| 6,168,430 B1 | 1/2001 | Higgins |
| 6,361,314 B1 | 3/2002 | Garton, Jr. |
| 6,394,799 B1* | 5/2002 | Testa ............... A61C 7/00 433/19 |
| 6,461,157 B1 | 10/2002 | Kussick |
| 6,669,474 B2 | 12/2003 | Vogt |
| 6,776,614 B2 | 8/2004 | Wiechmann |
| 6,913,460 B2 | 7/2005 | Cleary |
| 8,257,080 B2 | 9/2012 | Wiechmann |
| 9,101,437 B2* | 8/2015 | Ziehmer ............. A61C 7/36 |
| 2002/0132207 A1 | 9/2002 | Tuneberg |
| 2004/0157184 A1* | 8/2004 | Reising ............. A61C 7/14 433/8 |
| 2005/0158686 A1 | 7/2005 | Wiechmann |
| 2007/0026357 A1* | 2/2007 | Farber ............. A61C 7/36 433/18 |
| 2009/0035715 A1 | 2/2009 | Cleary |
| 2010/0285422 A1* | 11/2010 | Wiechmann ......... A61C 7/36 433/18 |
| 2011/0269094 A1 | 11/2011 | Shearer |
| 2012/0028207 A1 | 2/2012 | Cleary |
| 2012/0028208 A1 | 2/2012 | Cleary |

FOREIGN PATENT DOCUMENTS

| | | |
|---|---|---|
| DE | 10346489 | 5/2004 |
| DE | 202012012376 | 3/2013 |
| EP | 588961 | 3/1994 |
| EP | 1108397 | 6/2001 |
| EP | 1976450 | 10/2008 |
| FR | 2760631 | 9/1998 |
| WO | WO 1998-53754 | 12/1998 |
| WO | WO 2004-39276 | 5/2004 |
| WO | WO 2005-5079694 | 9/2005 |
| WO | WO 2007-014144 | 2/2007 |
| WO | WO 2012-18648 | 2/2012 |
| WO | WO 2012-40490 | 3/2012 |
| WO | WO 2012-74846 | 6/2012 |
| WO | WO 2013-96090 | 6/2013 |

* cited by examiner

LABIAL ATTACHMENT DEVICE FOR USE WITH ORTHODONTIC AUXILIARY AND LINGUAL APPLIANCE SYSTEM

CROSS REFERENCE TO RELATED APPLICATIONS

This application is a national stage filing under 35 U.S.C. 371 of PCT/US2014/068071, filed Dec. 2, 2014, which claims the benefit of European Application No. 13195992.6, filed Dec. 6, 2013, the disclosure of which is incorporated by reference in its/their entirety herein.

BACKGROUND

The field of orthodontics relates to the supervision, guidance and correction of teeth towards proper positions in the oral cavity. Orthodontic therapy generally involves the application of forces to move teeth into a proper bite configuration, or occlusion. One mode of therapy, known as fixed appliance treatment, is carried out using a set of tiny slotted appliances called brackets, which are affixed to at least the anterior, cuspid, and bicuspid teeth of a patient. In the beginning of treatment, a resilient orthodontic appliance known as an archwire is received in each of the bracket slots. The end sections of the archwire are typically anchored in appliances called buccal tubes, which are affixed to the patient's molar teeth.

When initially installed in the brackets and buccal tubes, the archwire is deflected from its original arcuate (or curved) shape, but then gradually returns to this shape during treatment. In this manner, the archwire applies gentle, therapeutic forces to move the teeth from improper positions to proper positions. Taken together, the brackets, buccal tubes, and archwire are commonly referred to as "braces". Braces are often prescribed to improve dental and facial aesthetics, bite function and dental hygiene. In many instances, a set of brackets, buccal tubes and an archwire is provided for each of the upper and lower dental arches.

Brackets and other components of the fixed appliance system are commonly placed on the labial (i.e., near the patient's lips and cheeks) surfaces of the teeth. In recent decades, advances in the art have enabled brackets to be placed on the lingual surfaces of teeth. Accordingly, the components of the fixed appliance system, including the archwire, are disposed nearer the tongue, providing an attractive, aesthetic alternative as the appliance system is essentially hidden from view. Lingual brackets often have a customized design individually for every tooth and patient because, other than the labial surfaces of a tooth, the lingual surfaces greatly vary in shape relative to each other so that a "one size fits all" bracket shape typically cannot be used. Exemplary appliance systems that include brackets customized to the lingual surfaces of a dental arch are disclosed in US Publication No. 2005/0158686 (Wiechmann et al.).

During certain stages of treatment, additional intraoral appliances may be prescribed for use in conjunction with fixed appliances to correct particular kinds of malocclusions. For example, some appliances are used to correct Class II malocclusions, such as an overbite where the mandibular first molars are located excessively distal (in the rearward direction) with respect to the maxillary first molars when the jaws are closed. Other appliances remedy an opposite malocclusion, known as a Class III malocclusion, such as an underbite where mandibular first molars are located excessively mesial (in the forward direction) with respect to the maxillary first molars when the jaws are closed.

In recent years, Class II and Class III correctors have been developed that are installed by the orthodontist and require minimal patient intervention during the course of treatment. These devices advantageously correct Class II and Class III malocclusions without need for patient compliance. A number of intra-oral devices for correcting Class II and Class III malocclusions are known in the art. For example, U.S. Pat. Nos. 4,708,646, 5,352,116, 5,435,721, 5,651,672, and 8,257,080 describe intra-oral bite correctors with flexible members that are connected to upper and lower arches of a patient. The length of the bite corrector is selected such that the member is curved in an arc when the patient's jaws are closed. An inherent bias tends to urge the members toward a normally straight orientation and provide a force that pushes one dental arch forward or rearward relative to the other dental arch when the jaws are closed.

Moreover, there are various possibilities in connecting these devices to the dental arch. Banded headgear tubes are still commonly used to provide a distal connection to the upper dental arch. These banded appliances, however, are not universally used. Bondable molar appliances are more convenient to use with labial systems in many respects and some orthodontists prefer them over banded appliances. As another option, connection to the dental arch may be made indirectly by coupling the intraoral device to one or both archwires.

SUMMARY

Though myriad products and solutions exist for attaching the Class II and Class III correctors to labial braces, the same cannot be said for lingual appliance systems. Typical methods of attachment are reliant on the presence of an archwire and other appliances on the labial surfaces of the patient's dental arches to provide an anchor for the outer end of the corrector. In present lingual appliance systems, the archwire is located proximate the lingual surfaces of the tooth, rendering attachment of the outer end loop impossible without further intervention. Furthermore, the common loop configuration used to couple the mesial end to the aforementioned correctors to the archwire tends to allow rotation of the certain components of the corrector in directions away from the tooth, about a generally mesial-distal reference axis. Such rotation increases the profile of the corrector and engages the patient's cheeks, causing discomfort and potentially decreasing compliance.

The present disclosure provides an assembly and system allowing for secure use of orthodontic auxiliaries, particularly bite correctors, with lingually bonded appliance systems. In one aspect, the disclosure features an orthodontic assembly including a banded tube, a force module, a connector coupling the force module to the tube, and an attachment device secured to the labial surface of an anterior tooth and connected to mesial, outer end of the force module. The outer end includes one or more loops engaged with a mounting bar on the attachment device. The mounting bar includes a defined recess for receipt of the loop configuration, with the boundaries of the recess designed to reduce or prevent undesired rotation of the force module. The attachment device thus enables the force module to be coupled or otherwise connected to the lower dental arch in the absence of an archwire or other labially bonded bracket. The assembly further serves to reduce the profile of labially attached bite correctors during use; increasing patient comfort and likely compliance with the prescribed treatment.

In one aspect, the present disclosure provides an orthodontic assembly for applying therapeutic forces between a patient's upper and lower dental arches that includes a connector for coupling to an upper arch appliance; a first attachment device secured to an anterior tooth and comprising a mounting bar and a base; and a force module having two opposing ends, with one end coupled to the connector and the opposite end adapted for coupling to the mounting bar of the attachment device. In some implementations, the mounting bar includes a mesial-distal segment and a biasing segment, the biasing segment extending at an acute angle relative to the mesial-distal segment, with the two segments defining a recess. The opposite end of the module can include a loop configuration, and a least a portion of the loop configuration can be received in the recess. The mesial-distal segment and the biasing segment cooperate to limit rotation of the force module about a generally mesial-distal reference axis. The assembly may further include a second attachment device secured to a tooth surface, wherein the second attachment device is ligated or otherwise coupled to the first attachment device.

In another aspect, the present disclosure provides an orthodontic assembly comprising a set of brackets coupled to the lingual surfaces of a patient's dental arch and a wire connected to the brackets. The assembly further includes a connector for coupling to an upper arch appliance; a first attachment device secured to a labial surface of an anterior tooth and comprising a mounting bar and a base; and a force module having two opposing ends, with one end coupled to the connector and the opposite end adapted for coupling to the mounting bar of the attachment device. In some implementations, the mounting bar includes a mesial-distal segment and a biasing segment, the biasing segment extending at an acute angle relative to the mesial-distal segment, with the two segments defining a recess. The opposite end of the module can include a loop configuration, and a least a portion of the loop configuration can be received in the recess. The mesial-distal segment and the biasing segment cooperate to limit rotation of the force module about a generally mesial-distal reference axis. The assembly may further include a second attachment device secured to a tooth surface, with the second attachment device ligated or otherwise coupled to the first attachment device. The upper arch appliance may include a band having a surface with a contour that approximates or matches the contour of an occlusal surface of a molar tooth.

In another aspect, the present disclosure provides a kit. In some embodiments, the kit includes one or more assemblies including: a connector for coupling to an upper arch appliance; a first attachment device comprising a mounting bar and a base; and a force module having two opposing ends, with one end coupled to the connector and the opposite end adapted for coupling to the mounting bar of the attachment device. Optionally, the kit can further include instructions for using the assemblies as described herein. Optionally the kit can further include a banded tube for securing to a posterior tooth. Optionally the kit can further include a hardenable dental composition, for example, that can be used to bond the attachment device to a labial tooth structure as described herein. In certain embodiments, the hardenable dental composition is an unfilled or lightly filled composition (e.g., a primer or a self-etching primer). In other certain embodiments, the kit further includes a self-etching primer, for example, that can be applied to the tooth structure prior to bonding the attachment device to the tooth structure. The kit may optionally include a second attachment device and a ligature.

As used herein: "Mesial" means in a direction toward the center of the patient's curved dental arch; "Distal" means in a direction away from the center of the patient's curved dental arch; "Occlusal" means in a direction toward the outer tips of the patient's teeth; "Gingival" means in a direction toward the patient's gums or gingival; "Facial" means in a direction toward the patient's lips or cheeks; and "Lingual" means in a direction toward the patient's tongue.

As used herein, "height of contour" means the point of greatest convexity of a tooth.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF EXEMPLARY EMBODIMENTS

The term "orthodontic auxiliary", as used herein, is defined as any accessory device or appliance that facilitates the application of forces in orthodontic treatment. Primary auxiliaries include bite correctors or force modules that apply therapeutic forces between two or more locations in the oral cavity. Auxiliaries used in Class II and Class III correction, for example, often employ force modules acting between appliances located on the upper and lower arches. However, auxiliaries may also exert and/or direct forces between two different portions within the same arch. As further alternative, auxiliaries may direct and/or exert forces between a wire and a fixed appliance such as a bracket, or between a bracket and a temporary anchorage device such as a mini-screw implant.

Figure 1:
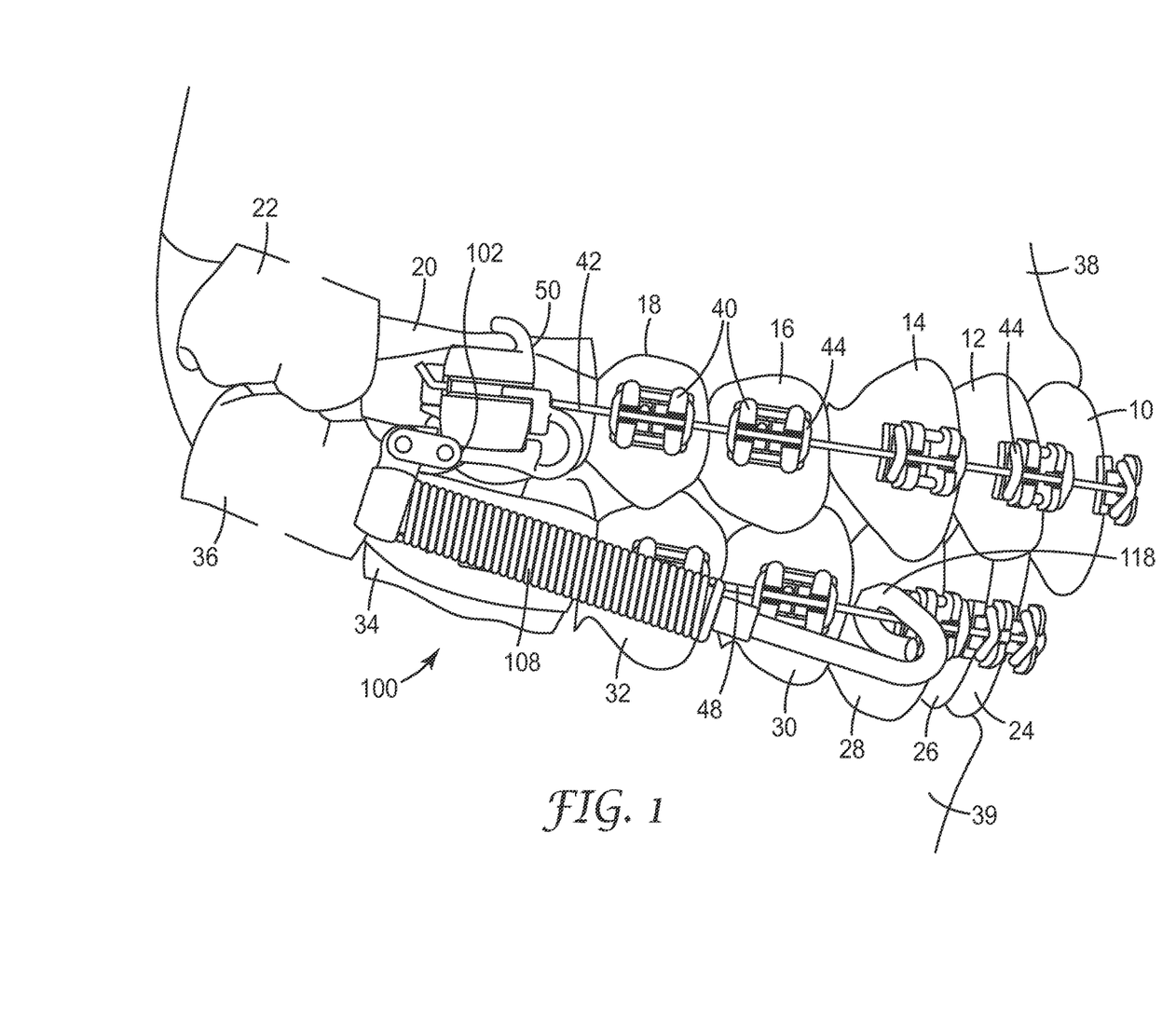
FIG. 1 is a side elevational view of an exemplary upper and lower dental arch of a patient undergoing orthodontic treatment that includes the use of a labial bracket system and an interarch force module.
Figure 2:
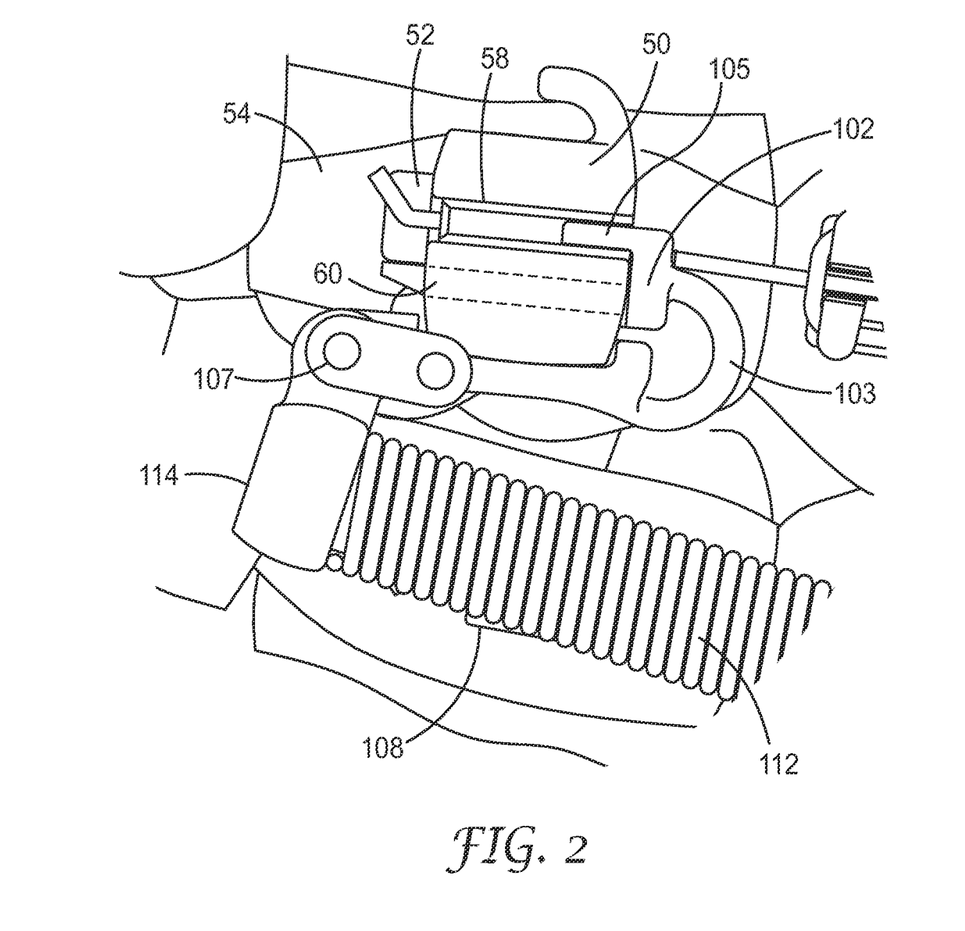
FIG. 2 is an enlarged elevational view of a connector and buccal tube appliance depicted in FIG. 1, looking at the connector and the buccal tube appliance in a lingual direction.

An exemplary embodiment of a typical, labially anchored intraoral appliance system is shown in FIGS. 1 and 2. These figures depict an orthodontic assembly, which is designated herein by the numeral 100. The assembly 100 is installed on the right side of the upper and lower jaws (38, 39) of a patient, which are illustrated in profile view. As shown, the teeth of the upper jaw 38 include an upper central 10, upper lateral incisor 12, upper cuspid 14, upper first bicuspid 16, upper second bicuspid 18, upper first molar 20, and upper second molar 22. Similarly, the teeth of the lower jaw include a lower central 24, lower lateral 26, lower cuspid 28, lower first bicuspid 30, lower second bicuspid 32, lower first molar 34 and lower second molar 36.

A number of slotted orthodontic appliances (i.e., brackets) 40 are fixed to the teeth of the patient's upper jaw 38 and an archwire 42 is received in the archwire slot of each appliance 40. An elastomeric O-ring ligature 44 extends around tiewings of each bracket 40 in order to retain the archwire 42 in the archwire slots of the brackets 40. Similarly, a number of slotted orthodontic brackets 46 are fixed to the teeth of the patient's lower jaw 39. An archwire 48 is received in the slot of each bracket 46. An elastomeric O-ring ligature extends around the tiewings of each bracket 46 in order to retain the archwire 48 in the archwire slots of the brackets 46. In this example, both upper and lower wires 42, 48 have generally rectangular cross-sections in planes perpendicular to their longitudinal axes. Other archwire configurations, including ovular and circular cross-sections, are also possible.

The right distal end of the upper archwire 42 is received in an archwire slot of a buccal tube appliance 50. Optionally, an end section of the archwire 42 is bent as shown in FIGS. 1 and 2 in a location adjacent the distal side of the buccal tube appliance 50. Each bracket and buccal tube includes a base for bonding the appliance to the facial surface of its respective tooth.

The buccal tube appliance 50 includes a base 52. In the illustrated example, the base 52 is affixed to a band 54. The band 54 encircles the patient's upper right first molar tooth 20 and is connected to the buccal tube appliance 50 by a weld or a braze joint. Optionally, the buccal tube appliance 50 may be connected to the molar tooth 20 by other means such as an adhesive bond between the base 50 and the enamel surface of the molar tooth 20. The buccal tube appliance 50 has a body 56 that extends outwardly from the base 50 in a generally facial direction and includes an archwire slot 58. The body 56 includes a passage 60 adjacent the archwire slot 58. In certain implementation further described herein, the passage 60 is used in coupling a force module 108 to the buccal tube appliance 50.

The assembly 100 includes a combination of elements that cooperate in applying a therapeutic force between the upper and lower dental arches. In the embodiment shown, the assembly 100 includes a connector 102 and a force module 108, which are coupled to the upper buccal tube 50 and lower wire 48, respectively. As depicted in FIGS. 1 and 2, the connector 102 is coupled to the passage 60 in the buccal tube appliance 50. On the end opposite the connector 102, the force module 108 is coupled to the lower wire 48 between the lower cuspid bracket and lower first bicuspid bracket.

Preferably, the force module 108 shares aspects with the bite corrector described in U.S. Pat. No. 5,964,588 (Cleary). In brief, the force module 108 includes a first elongated tubular member, a second elongated tubular member that is received in the first member in sliding, telescoping relation, and a third member 110 that is received in the second member. A helical compression spring 112 extends around the first tubular member and has an outer end that bears against a distal end cap 114 of the force module 108 that is fixed to the first member. The opposite end of the spring 112 bears against an annular fitting 116 that is secured to an outer end section of the second member.

Typically, the outer mesial end 118 of the third member 110 is formed into a loop-type configuration as shown in FIG. 1 that extends around a section of the lower wire 48. Additional examples of loop-type configurations are set out in U.S. Pat. No. 6,669,474 (Vogt). In some embodiments, the outer end 118 of the third member 110 also includes a line of weakness such as a recess or other area of reduced thickness for ease of bending the outer end section around the lower wire 48. Alternatively, the outer mesial end may be coupled to the lower archwire via resilient link, as exemplified in US Publication No. 2012/0028208 (Cleary) Examples of suitable commercially-available force modules 108 include the FORSUS brand fatigue resistant Class II correctors from 3M Unitek Corporation (Monrovia, Calif.).

The overall effective length of the force module 108 is typically selected so that the first and second members are not fully compressed and the second member is not fully inserted into the first member when the patient's jaws 38, 39 are closed. As a consequence, the inherent bias of the spring 112 provides the desired corrective forces by urging the first and second member away from each other in order to move one dental arch relative to the other.

As shown in more detail in FIG. 2, a connector 102 includes a first post that extends through the opening of the end cap 114. The first post is pivotally movable in the opening and enables pivotal movement of the connector 102 relative to the force module 108 in an arc about a facial-lingual reference axis. The connector 102 also includes a second post that is spaced from and parallel to the first post. A flat, oval-shaped plate 107 is coupled to the outer ends of both posts and serves to retain the connector 102 in secure, coupled relationship to the end cap 114.

The connector 102 typically includes at least one resilient portion 103 that enables the connector 102 to couple to the upper buccal tube appliance 50 in a "snap-fit" relationship. This "snap-fit" relationship is similar to the "snap-fit" relationship described in connection with the orthodontic attachment modules and couplings described in U.S. Pat. No. 6,913,460 (Cleary et al.) and U.S. Patent Application Publication No. 2009/0035715 (Cleary). The resilient portions tend to hold the connector 102 in place and in captive relationship to the buccal tube appliance 50 during the course of treatment, but also enable the connector 102 to be disconnected from the buccal tube appliance 50 when desired.

Preferably, the connector 102 includes at least one rotation stop 105 that helps limit undue rotational movement of the connector 102 and hence of the force module 108 about a reference axis extending in a generally mesial-distal direction. In certain circumstances, the connector 102 includes two rotation stops that are movable relative to each other in order to facilitate placing the rotation stops in certain beneficial operative positions adjacent wall structures of the buccal tube appliance 50 for further limiting undue rotational movements. Additional aspects and alternative constructions regarding the connector 102 are set out in the aforementioned U.S. Patent Application Publication No. 2009/0035715 (Cleary), particularly the connectors depicted in FIGS. 11 and 12. As additional alternatives, the force module 108 may be coupled to the upper arch by the connector described in US Publication No. 2012/0028207 (Cleary et al.), which features connectors coupled to an upper wire between the upper second bicuspid bracket and the upper buccal tube. In operation, such alternative connectors slide distally along the wire until bearing against the mesial side of buccal tube, while the third member of a force module slides mesially along the lower archwire until it bears against the distal side of a lower arch bracket.

As can be appreciated by reference to FIGS. 1 and 2, the orthodontic assembly 100 is reliant on the presence of an archwire and other appliances on the labial surfaces of the patient's dental arches to provide an anchor for the outer end of third member 118 and the connector 102. In present lingual appliance systems, such as those described in U.S. Pat. No. 6,776,614 (Wiechmann et al.), the archwire and brackets are not available proximate the labial tooth surfaces, rendering attachment of the outer end loop impossible without further intervention.

Figure 3:
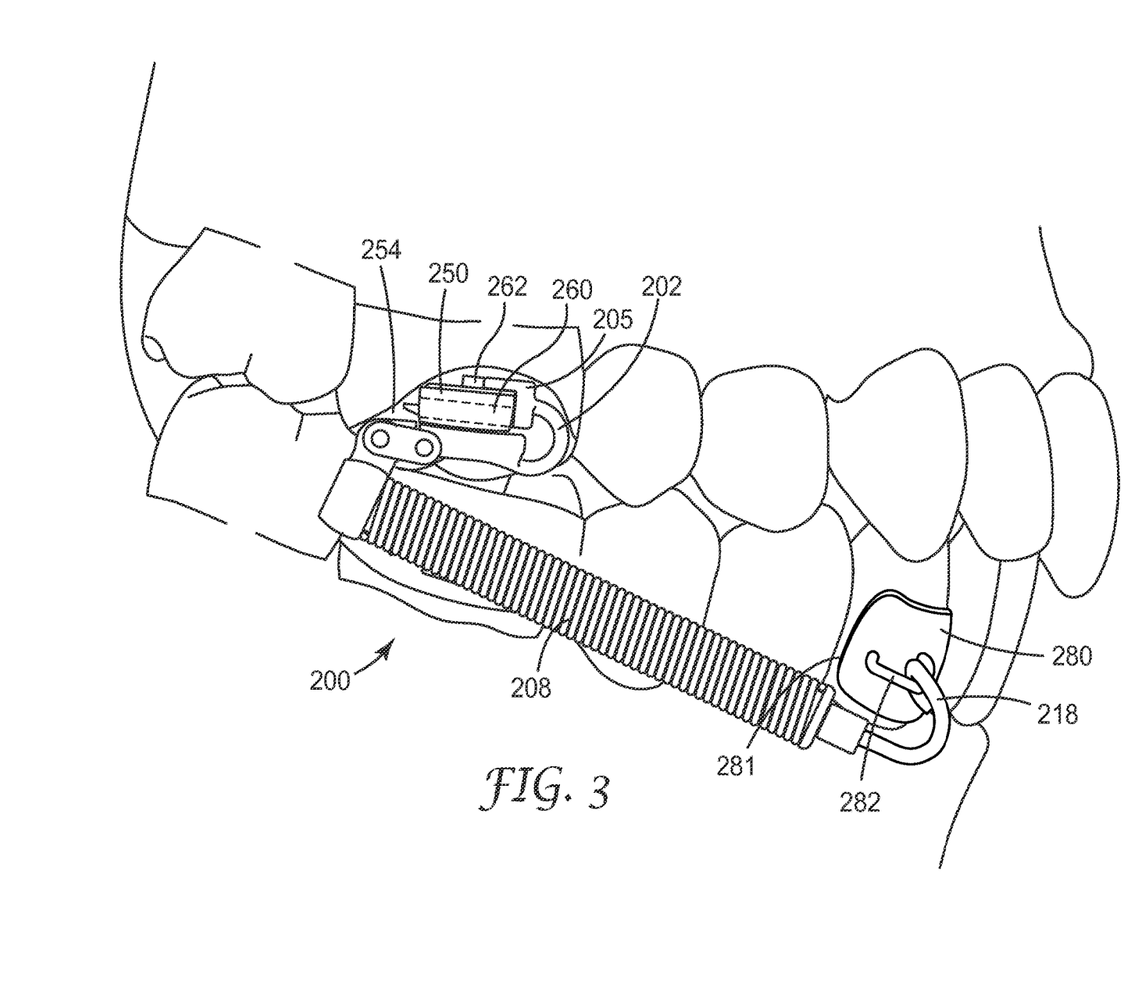
FIG. 3 is a side elevational view of an exemplary upper and lower dental arch of a patient undergoing orthodontic treatment that includes use of an interarch force module coupled to an anterior teeth via an attachment device according to one embodiment of the disclosure.
Figure 4:
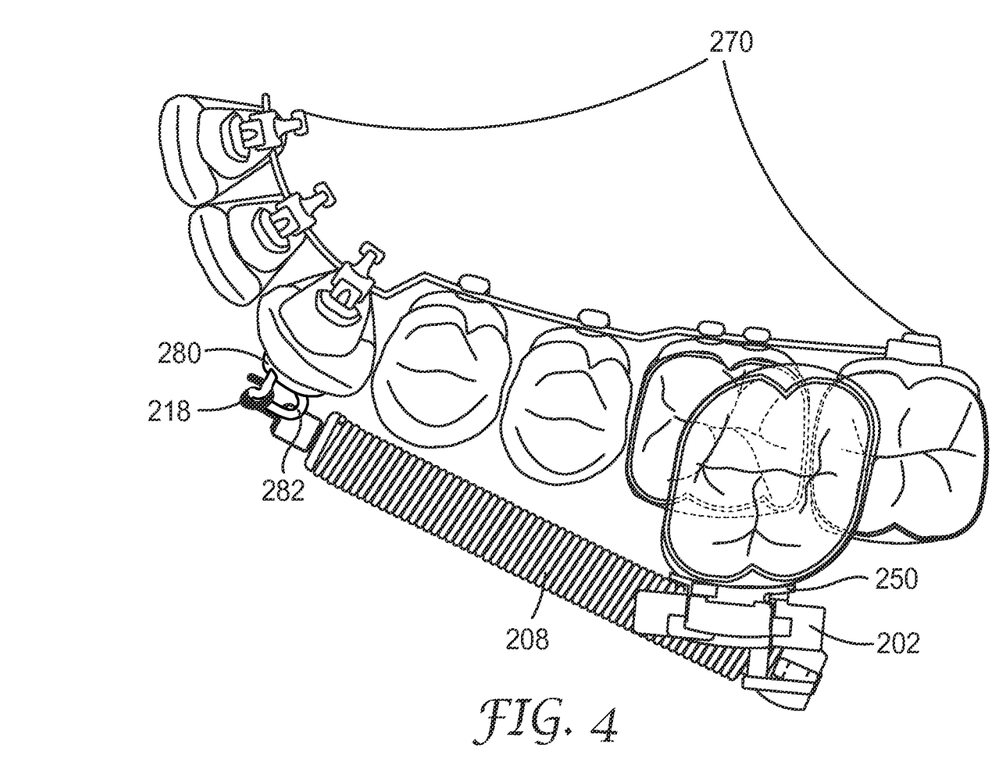
FIG. 4 is a fragmentary plan view of the dental arches and the force module shown in FIG. 2, except that some of the patient's upper teeth and associated orthodontic appliances have been omitted from the view for purposes of illustration.

FIGS. 3 and 4 illustrate an assembly 200 for coupling an orthodontic auxiliary, used in cooperation with a lingual appliance system 270 (shown only in FIG. 4), to the labial side of a patient's dental arch. The assembly 200 includes a force module 208, a banded tube 250, an attachment device 280, and a connector 202. Many aspects of the connector 202, banded tube 250, and force module 208 are similar to those components illustrated in FIGS. 1 and 2, and the same numbering system is utilized to denote common features.

The banded tube 250 includes a band 254 that at least partially encircles the upper first molar tooth, generally above the height of contour. A band that encircles a portion to the molar tooth substantially below the height of contour may, in certain circumstances, interfere with the bonding of desired appliances to the lingual surface of the molar. The band 254 can extend above the height of contour and over the occlusal surfaces of molar tooth. In such implementations, the band 254 may include a surface having a contour that approximates or matches the contour of an occlusal surface of the molar tooth, including all or a portion of the facial and lingual cusps. These complementary contours can offer an improved fit between the banded tube 250 and the first molar tooth.

The banded tube 250 further includes a body extending in a generally facial direction from a base 252. The body includes a passage 260 defined therein and configured for receipt of a shank or other segment from the connector 202. Unlike buccal tube appliance 50, the body 256 lacks an archwire slot located in a gingival direction from the passage. As with the buccal tube appliance 50, however, the banded tube 250 may be connected to the molar tooth by other means such as an adhesive bond between the base 252 and the labial surface of the molar tooth.

The body 256 further includes a rotation stop 262 projecting from an exterior surface, in the direction of the gingival tissue of the upper arch. The rotation stop 262 includes a generally flat surface that, when the body 256 is coupled to connector 202, engages with rotation stop 205 to limit undue rotational movement of the connector 202 and the force module 208 about a reference axis extending in a generally mesial-distal direction. The engagement of the rotation stop structures 205, 262 assists in maintaining the force module 208 in a lower profile configuration adjacent the wearer teeth.

A mesial outer end 218 of the force module 208 is connected to an attachment device 280, which is secured to the labial surface of an anterior tooth. The outer end 218 in this implementation is configured in one or more loops engaged with a mounting bar 282 positioned on the attachment device 280. The attachment device 280 thus enables the force module 208 to be coupled or otherwise connected to the lower dental arch. As depicted, the attachment device 280 is secured to the lower cuspid tooth. In other environs, however, the attachment device 280 may be placed on a first bicuspid or lateral incisor of the lower arch, with the loop configuration and/or length of the third member adjusted accordingly. In other yet other embodiments, the attachment device can be place on a second bicuspid.

Figure 5:
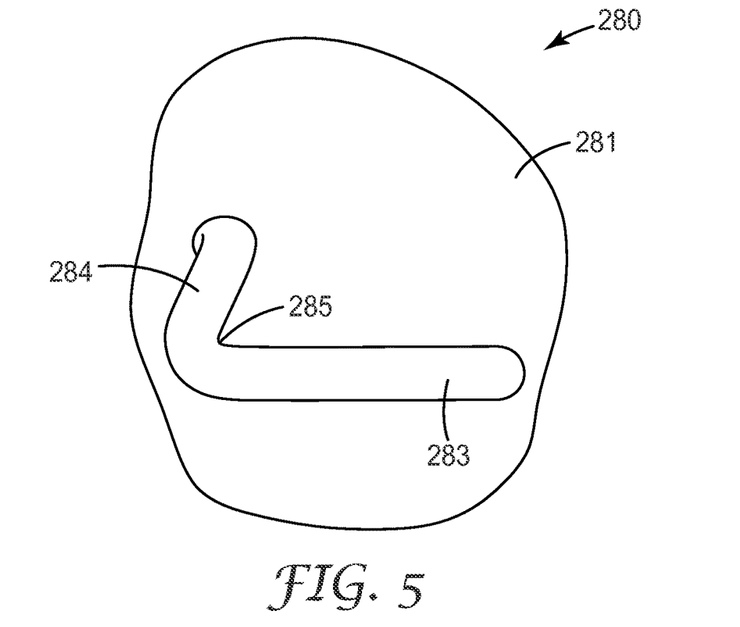
FIG. 5 is an isometric view of a labial attachment device according to one embodiment of the present disclosure.
Figure 6:
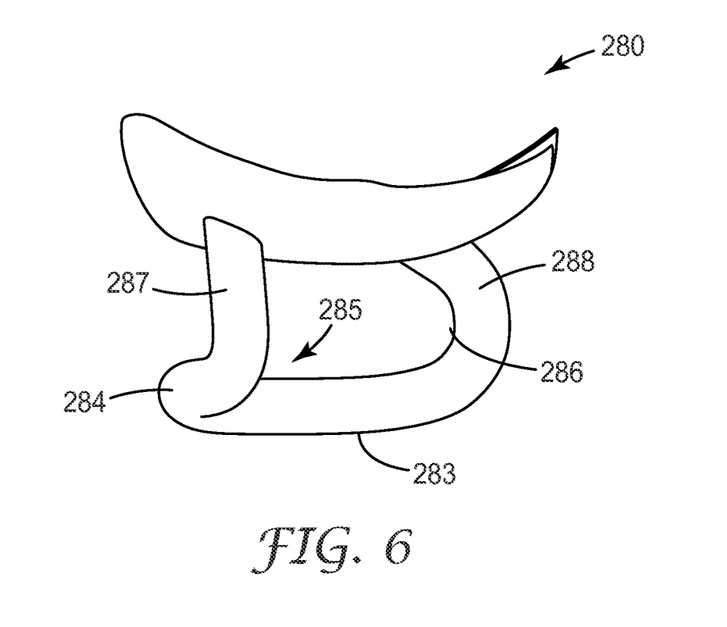
FIG. 6 is a top view of the labial attachment device of FIG. 4.

An exemplary attachment device 280 is illustrated in FIGS. 5 and 6, and includes a base 281 and a mounting bar 282 offset from the base 281. The mounting bar 282 includes a cross-sectional dimension sufficient to withstand forces exerted by the force module without substantial deformation or decoupling from the base 281. As depicted, the mounting bar 282 includes a longitudinal cross-section having a generally circular shape. The mounting bar 282 can also exhibit other shapes in longitudinal cross-section, including, for example, ovular, quadrate, and rectangular. In presently preferred circumstances, the mounting bar 282 has a largest cross-sectional dimension of at least 0.8 mm and no greater than 1.5 mm.

The mounting bar 282 encompasses a lateral segment 283, extending in a generally mesial-distal direction (as depicted in FIG. 5) across the surface of the base 281 and a biasing segment 284, bent and extending at an acute angle relative to the lateral segment 283. Though not presently preferred, the biasing segment 284 can create an obtuse angle with the lateral segment 283; some of the benefits of the acute arrangement detailed below, however, may not be realized. The biasing segment 284 is depicted in the Figures as extending in a direction towards the occlusal surfaces of the dental arch; other implementations of the present disclosure can feature a biasing segment extending towards the gingiva. The mounting bar 282 is typically placed at a location on the base 281 such that the lateral segment 283 will be closer to the gingival tissue than an occlusal tooth surface when the attachment device 280 is secured to the desired tooth. Locating the lateral segment 283 nearer the gingiva reduces the likelihood that the attachment device 280 will engage with a tooth of the opposing dental arch. Such interference can, in certain circumstances, result in substantial patient discomfort.

The lateral segment 283 and the biasing segment 284 cooperate to define a first recess 285. When the attachment device 280 is secured to a tooth, the first recess 285 is typically located in a mesial direction relative to the lateral segment 283. During use of the orthodontic assembly 200, a loop or similar bend of the outer end 218 of force module 208 is received within or in close proximity to the recess 285. The boundaries of the recess 285 (e.g., portions of the mounting bar and, in certain circumstances, the exterior surface of base 281) limit or prevent the outer end 218 from rotating in directions away from the tooth, or about a mesial-distal reference axis relative to the base 281. As outward rotation increases the profile of the force module 208, the likelihood of unintended force module interference with the wearer's cheeks and resultant discomfort can be dramatically reduced.

A pair of spaced apart struts 287, 288 act to couple the mounting bar 282 to the base 281. In typical implementations, the struts 287, 288 are integrally formed with the mounting bar 282. It is also contemplated, however, that the struts 287, 288 are integrally formed with the base 281 and welded or brazed to the mounting bar 282. The lateral segment 282 and second strut 288 cooperate to define a second, annular recess 286. In certain implementations, the second recess 286 can limit or prevent unintended distal detachment of the outer end 218 of the force module 286.

The base 281 can be a flange made of metal, plastic, ceramic, and combinations thereof. Alternatively, the base 281 can be a custom base formed from cured adhesive layer(s) (i.e., single or multi-layer adhesives). The base 281 includes a tooth facing surface that approximates or reflects the contour of an anterior or posterior labial tooth surface. The base 281, the mounting bar 282, and struts 287, 288 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 281, the mounting bar 282, and struts 287, 288 are integrally made as a unitary component. In another embodiment, the base 281 may include two or more base segments, with each strut 287,288 coupled to its own base segment instead of sharing a common base.

An exemplary possibility for providing an attachment device 280 with a customized base 281 is described in US Publication No. 2005/0158686. The base design may be performed on a computer that stores a three-dimensional virtual dental arch of a patient. The virtual dental arch may be obtained by scanning the patient's teeth or a physical model of the patent's teeth, thus digital data file including a representation of one or more dental arches. The computer may be equipped with treatment planning or appliance positioning software, or placing the attachment device at a desired location on the tooth surface, respectively. The tooth facing base geometry (i.e., bonding surface) may be derived directly from tooth geometries represented in the virtual dental arch so that the base obtains a three-dimensional surface which substantially exactly matches with the corresponding tooth surface. The term "substantially exactly" in this regard means that the surfaces are identical except for the eventual presence of tolerance deviations that may result from making the pad. This allows for a relatively precise placement of the attachment device on the tooth and helps in maximizing the bonding strength.

Components of the assembly 200 and the attachment device 281 may be manufactured according to any number of methods known to the skilled artisan. These methods include, but are not limited to, milling, investment casting, metal injection molding, and rapid prototyping. If desired, one or more of these components can also be manufactured from other classes of materials, such as ceramics, polymers, or composites. If polymeric components are used, these may optionally be formed by milling, injection molding, extrusion or additive manufacturing. Examples of suitable additive manufacturing processes include solid freeform fabrication such as 3D printing processes, stereolithography methods, fused deposition modeling, laminated object manufacturing, laser engineered net shaping, selective laser sintering, shape deposition manufacturing, selective laser melting, and solid ground curing. An example of a suitable 3D printing machine is the Eden brand 500V printer from Objet Geometries Ltd., using FullCure 720 acrylic-based photopolymer printing material (also available from Objet Geometries Ltd.).

In certain embodiment, the mounting bar 282 may be created separately from the base 281 and thereafter welded or otherwise coupled to the exterior surface. For example, a wire of suitable thickness, strength and resilience may be crimped to create the appropriate segments and recesses, and thereafter bond to the base 281. In another example, a suitable wire may be secured to the pad at two locations and thereafter crimped to create the desired struts and recesses.

Compositions useful in bonding the attachment device 280 to the tooth enamel are well known to those skilled in the art. Suitable hardenable dental compositions include orthodontic adhesives such as composites, compomers, glass ionomers and resin-modified glass ionomers. Examples of light-curable adhesives include Transbond XT brand and Transbond PLUS brand adhesives from 3M Unitek Corporation (Monrovia, Calif.). Examples of chemical curing adhesives include Concise brand adhesive and Unitek™ Multi-Cure brand glass ionomer cement from 3M Unitek Corporation.

The tooth structure of the attachment device target site can be untreated or treated. In some embodiments, the tooth structure is treated with a self-etching primer prior to contacting 281 with the tooth structure. For such embodiments, the hardenable dental composition can typically be hardened during or immediately after compressing the compressible material. In some embodiments, the hardenable dental composition is self-etching, and the tooth structure can be untreated prior to applying the attachment device 281. For such embodiments, the hardenable dental composition preferably contacts the tooth structure for a period of time (e.g., 15 seconds or more) prior to hardening the hardenable dental composition. As an alternative, the tooth structure can be treated by phosphoric acid etching, followed by priming with a suitable orthodontic primer such as TRANSBOND XT brand primer or TRANSBOND MIP brand primer (both from 3M Unitek, Monrovia, Calif.).

Relatively large intra-oral forces are often applied to orthodontic components during movement of the jaws. For example, the forces generated when chewing can be significant, especially when the patient bites into a hard food object such as hard candy, nuts or ice. The chewing forces can be especially large in molar regions of the patient's jaws, and hard food objects can transmit the forces to the attached orthodontic components. In some instances, the forces can break the components or cause the components to spontaneously detach from the teeth such that the progress of treatment is interrupted. These components may be accidentally consumed by the wearer, or may cause damage to the cheeks or gingival tissue when untethered to the dental arch.

Figure 7:
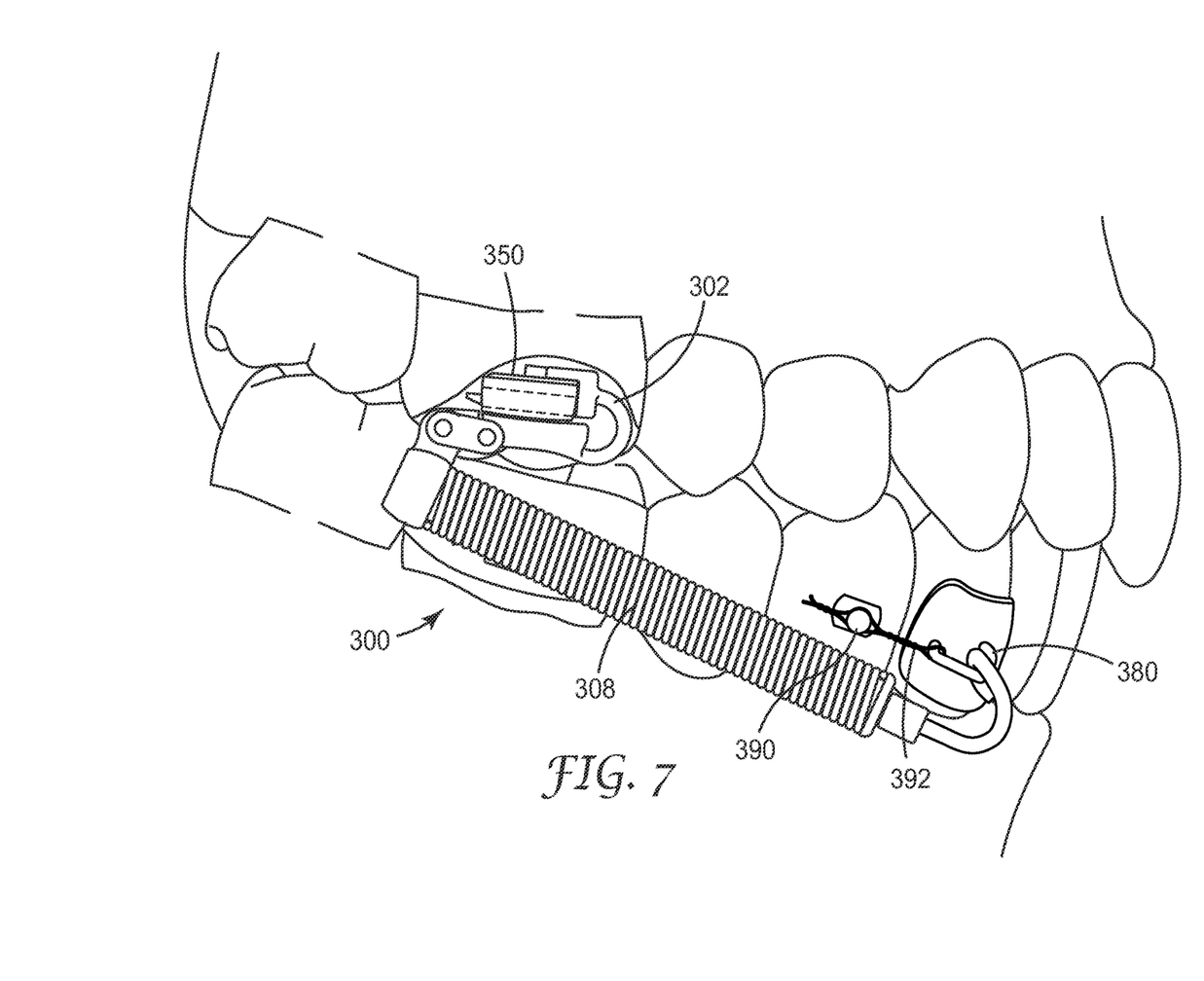
FIG. 7 is a side elevational view of an exemplary upper and lower dental arch of a patient undergoing orthodontic treatment that includes use of an interarch force module coupled to the anterior tooth via an attachment device according to another embodiment of the disclosure.

Such issues are at least partly addressed by the orthodontic assembly 300 depicted in FIG. 7. The assembly 300 includes a force module 308, a banded tube 350, a connector 302, and an attachment device 380. Many aspects of the connector 302, force module 308, banded tube 350, and attachment module 380 are similar to those components illustrated above and are not separately discussed further. The orthodontic assembly 300 is distinguishable from prior assemblies due to the presence of a second attachment device 390 in the form of a button secured to a tooth in a distal relationship to attachment device 280. In the depicted implementation, the button 390 is secured to a lower, first bicuspid tooth surface. A ligature 392 is wound around the button 390 and coupled to the mounting bar 382 proximate the second recess 286. The ligature 392 may be a wire or elastomeric ring (e.g., O-ring, or one or more orthodontic power chain segments), but can conceivably comprise any material suitable for loosely attaching the button 390 to the mounting bar 282, including filamentous thread. Securing the attachment device 380 to another structure reduces the risk that components of the orthodontic assembly 300 (particularly the third member 318 and attachment device 390) can be swallowed or inhaled, even in the event of fracture or debonding. The relatively loose attachment provided by the ligature reduces the likelihood that any unwanted force between the two devices will interfere with prescribed treatment.

The second attachment device 390 can be positioned on a lingual tooth surface and the ligature between first and second attachment devices 380, 390 could be placed at an interdental (i.e., interproximal) position. In yet other implementations, the attachment device 380 could be secured via appropriate ligature to a lingual bracket, orthodontic archwire, or a combination of both. The lingual bracket and/or archwire used to anchor the attachment device 380 may be located on the same or a different tooth.

Although not shown in the drawings, the force modules and attendant orthodontic assemblies described herein are normally used in pairs. While the Figures depict the orthodontic assemblies in place along the left side of a patient's oral cavity, a second assembly that is similar to the depicted orthodontic assemblies in mirror image is typically installed along the right side of the patient's oral cavity. In this manner, a balanced amount of force is presented along both sides of the patient's jaws for repositioning the dental arches as desired.

In further alternative embodiments, one or more of the orthodontic correctors above are adapted to correct a Class III malocclusion. Such correction may be achieved, for example, by connecting the one end of the assembly to an attachment device secured to an anterior tooth of the upper arch and the other end of the assembly to a lower banded tube. As before, the connections between components benefit from the increased robustness and functionality provided by the present disclosure.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

The invention claimed is:

1. An orthodontic assembly for applying therapeutic forces between a patient's upper and lower dental arches in the absence of a labially bonded archwire, the orthodontic assembly comprising:
   a connector for coupling to an upper arch appliance;
   a first attachment device comprising a base having a tooth-facing surface adapted for bonding to a labial surface of an anterior tooth and comprising a facial surface and a mounting bar coupled to and spaced from the facial surface of the base the mounting bar comprising:
      a first end attached to the facial surface of the base by a first strut;
      a second end attached to the facial surface of the base by a second strut;
      a mesial-distal segment; and
      a biasing segment,
      wherein the mesial-distal segment and the biasing segment are between the first end and the second end, wherein the mesial-distal segment and the biasing segment cooperate to define a first recess, wherein the second strut cooperates with the mesial-distal segment to provide a second recess, wherein the biasing segment extends at an acute angle relative to the mesial-distal segment; and a force module having two opposing ends, with one end adapted for coupling to the connector and the opposite end adapted for coupling to the mounting bar of the first attachment device.

2. The orthodontic assembly of claim 1, wherein the opposite end of the force module includes a loop configuration, and wherein a least a portion of the loop configuration is received in the recess.

3. The orthodontic assembly of claim 1, wherein the mesial-distal segment and the biasing segment cooperate to limit rotation of the force module about a generally mesial-distal reference axis.

4. The orthodontic assembly of claim 1, wherein the first attachment device is adapted to be secured to a single cuspid tooth.

5. The assembly of claim 1, further comprising a second attachment device secured to a location distal from the first attachment device, wherein the second attachment device is connected to the first attachment device with a ligature.

6. The orthodontic assembly of claim 1, wherein the upper arch appliance is a banded tube including a body defining a passage and band configured to at least partially encircle a molar tooth, generally above the height of contour.

* * * * *